(12) United States Patent
Kawajiri et al.

(10) Patent No.: US 9,914,072 B2
(45) Date of Patent: Mar. 13, 2018

(54) PROCESS FOR OPERATING A SIMULATED MOVING BED REACTOR

(71) Applicant: GEORGIA TECH RESEARCH CORPORATION, Atlanta, GA (US)

(72) Inventors: Yoshiaki Kawajiri, Atlanta, GA (US); Andreas S. Bommarius, Atlanta, GA (US); Jungmin Oh, Atlanta, GA (US); Gaurav Agrawal, Atlanta, GA (US); Balamurali Sreedhar, Doraville, GA (US)

(73) Assignee: Georgia Tech Research Corporation, Atlanta, GA (US)

(*) Notice: Subject to any disclaimer, the term of this patent is extended or adjusted under 35 U.S.C. 154(b) by 0 days.

(21) Appl. No.: 15/316,542

(22) PCT Filed: Jun. 4, 2015

(86) PCT No.: PCT/US2015/034175
§ 371 (c)(1),
(2) Date: Dec. 6, 2016

(87) PCT Pub. No.: WO2015/187931
PCT Pub. Date: Dec. 10, 2015

(65) Prior Publication Data
US 2017/0216740 A1 Aug. 3, 2017

Related U.S. Application Data

(60) Provisional application No. 62/008,560, filed on Jun. 6, 2014.

(51) Int. Cl.
*B01D 15/18* (2006.01)
*C07C 67/08* (2006.01)
*C07C 67/56* (2006.01)

(52) U.S. Cl.
CPC .......... *B01D 15/1857* (2013.01); *C07C 67/08* (2013.01); *C07C 67/56* (2013.01)

(58) Field of Classification Search
CPC ..... B01D 15/1857; C07C 67/56; C07C 67/08; C07C 69/14
See application file for complete search history.

(56) References Cited

U.S. PATENT DOCUMENTS

| | | |
|---|---|---|
| 6,518,454 B1 | 2/2003 | Arumugam et al. |
| 2013/0116495 A1 | 5/2013 | Frey et al. |

OTHER PUBLICATIONS

Seidel-Morgenstern et al, Chemical Engineering Technology, New Developments in Simulated Moving Bed Chromatography, 2008, 31(6), pp. 826-837. (Year: 2008).*
Yu et al, Industrial & Engineering Chemical Research, Modeling, Simulation, and Experimental Study of a Simulated Moving Bed Reactor for the Synthesis of Methyl Acetate Ester, 2003, 42, pp. 6743-6754. (Year: 2003).*
International Search Report & Written Opinion for related PCT Application PCT/US2015/034175, dated Sep. 16, 2015 (12 pgs).
International Preliminary Report on Patentability for related PCT Application PCT/US2015/034175, dated May 3, 2016 (6 pgs).
Agrawal, et al., "Optimization of Reactive Simulated Moving Bed Systems with Modulation of Feed Concentration for Production of Glycol Ether Ester"; Journal of Chromatography, Vo. 1360 (Sep. 1, 2014) (24 pgs).
Schramm, et al., "Improved Operation of Simulated Moving Bed Processes Through Cyclic Modulation of Feed Flow and Feed Conentration"; Chemical Engineering Science, vol. 58, No. 23-24 (Dec. 1, 2003) (12 pgs).
Schramm, et al., "Simulated Moving Bed Process with Cyclic Modulation of the Feed Concentration"; Journal of Chromatography, vol. 1006, No. 1-2 (Jul. 18, 2003) (10 pgs).

\* cited by examiner

*Primary Examiner* — Paul A Zucker
(74) *Attorney, Agent, or Firm* — Brooks, Cameron & Huebsch, PLLC

(57) ABSTRACT

The present disclosure provides for a process for supplying a first reactant and a second reactant (reactants) to a simulated moving bed reactor (SMBR) at each step of a sequential repeating injection cycle, where the SMBR includes zones each having an injection point and each containing a solid separation media; reacting the reactants in the SMBR during the sequential repeating injection cycle (cycle) to form a first product; separating the first product in the SMBR with the solid separation media; and changing an amount of one or both of the reactants injected at one or more of the injection points of the SMBR during a step of the cycle. Changing the amount of the reactants can be done at each step of the sequential repeating injection cycle. Changing the amount can include changing an inlet concentration of the reactants injected at one or more of the injection points during each step of the cycle.

16 Claims, 12 Drawing Sheets

PROCESS FOR OPERATING A SIMULATED MOVING BED REACTOR

This application is a National Stage Application under 35 U.S.C. § 371 of International Application Number PCT/US2015/034175, filed Jun. 4, 2015 and published as WO 2015/187931 on Dec. 10, 2015, which claims the benefit to U.S. Provisional Application 62/008,560, filed Jun. 6, 2014, the entire contents of which are incorporated herein by reference in its entirety.

FIELD OF THE DISCLOSURE

The present disclosure relates generally to a process for operating a simulated moving bed reactor.

SUMMARY OF THE DISCLOSURE

The present disclosure provides for a process for supplying a first reactant and a second reactant to a simulated moving bed reactor (SMBR) at each step of a sequential repeating injection cycle, where the SMBR includes zones each having an injection point and each containing a solid separation media; reacting the first reactant and the second reactant in the SMBR during the sequential repeating injection cycle to form a first product; separating the first product in the SMBR with the solid separation media; and changing an amount of one or both of the first reactant and the second reactant injected at one or more of the injection points of the SMBR during a step of the sequential repeating injection cycle.

The present disclosure further provides for a process for supplying a first reactant and a second reactant to the simulated moving bed reactor (SMBR) at each step of the sequential repeating injection cycle, where the SMBR includes zones each having an injection point and each containing a solid separation media; reacting the first reactant and the second reactant in the SMBR during the sequential repeating injection cycle to form a first product and a second product; separating the first product from the second product in the SMBR with the solid separation media; and changing an amount of one or both of the first reactant and the second reactant injected at one or more of the injection points of the SMBR during a step of the sequential repeating injection cycle. For the process, changing the amount of one or both of the first reactant and the second reactant can be done at each step of the sequential repeating injection cycle. For the process, each step of the sequential repeating injection cycle has a predetermined time ($t_{step}$), and changing the amount of one or both of the first reactant and the second reactant can begin once a first percentage of $t_{step}$ is reached. For example, the first percentage of $t_{step}$ can be from 50 percent (%) to less than 100% of $t_{step}$. In an additional example, the first percentage of $t_{step}$ can be from 65% to 67% of $t_{step}$. Other values are possible.

For the process, changing the amount of one or both of the first reactant and the second reactant can be done two or more times during a step of the sequential repeating injection cycle. For the process, changing the amount of one or both of the first reactant and the second reactant can be done as a step change. Alternatively, changing the amount of one or both of the first reactant and the second reactant can be done as a linear change. An example of changing the amount includes changing an inlet concentration of one or more of the first reactant and the second reactant injected at one or more of the injection points of the SMBR during each step of the sequential repeating injection cycle.

The process can also include supplying the first reactant to the SMBR at a stoichiometric excess sufficiently large relative the second reactant that the first reactant acts as a desorbent for both a raffinate stream and an extract stream of the SMBR. When the first reactant is at a stoichiometric excess relative the second reactant (e.g., the second reactant in a stoichiometric deficit relative to the first reactant), the second reactant can react to extinction in the SMBR. The process of the present disclosure can also include portions of either the raffinate stream and/or the extract stream being returned to the SMBR for further use. For example, the process can include supplying a portion of at least one of the raffinate steam and the extract stream to at least one of the zones of the SMBR. The solid separation media in addition to helping to separate the reactants and products can also act as a catalyst for the reaction of the first reactant and the second reactant.

DETAILED DESCRIPTION OF THE DISCLOSURE

The present disclosure provides a process for operating a simulated moving bed reactor (SMBR). As discussed herein, the process of the disclosure allows for the use of a SMBR that may help to improve the efficiency of equilibrium-limited reactions. As additionally discussed herein, the process of using the SMBR according to the present disclosure also allows for simultaneous reaction and separation of both product(s) and byproduct impurities. The removal of the product(s) and the byproduct impurities enables improved conversion beyond the equilibrium limit, providing for improved yields and simplified downstream purification.

The concept of reactive chromatography that integrates both separation and reaction inside the column has been a subject of considerable attention for last few decades. Such mechanism can facilitate reversible reactions to go beyond their thermodynamic equilibrium and thus lead to more product formation. However, these processes are operated in a batchwise manner. Simulated moving bed reactor (SMBR), on the other hand, is a process that performs reactive chromatography in a continuous fashion. SMBR operations can provide economic benefit for equilibrium limited reversible reactions such as hydrolysis and esterification. In such operations, in situ separation of product(s) facilitates the reversible reactions to completion beyond thermodynamic equilibrium and also helps in obtaining product(s) of high purity. Although the advantage of SMBRs has been highlighted in numerous studies, there exist very few industrial applications because of the difficulty of development and design of such systems.

As provided herein, the present disclosure provides an alternative to conventional SMBR operation, where the amount of reactants fed to the SMBR (e.g., the concentration of the reactants) is kept constant. In the present disclosure, the amount of reactants fed to the SMBR varies with time, which may help to significantly increase the productivity of the reaction taking place in the SMBR. Potential applications for the present disclosure include condensations, such as aldol condensations, acylation reactions including esterification, transalkylation, transesterification, and amidation involving reaction of an amine with an acid, such as a carboxylic acid, as well as alkylation, hydration, dehydration, amination, etherification, hydrolysis, isomerization, and oligomerization. Other reactions are also possible.

Figure 1:
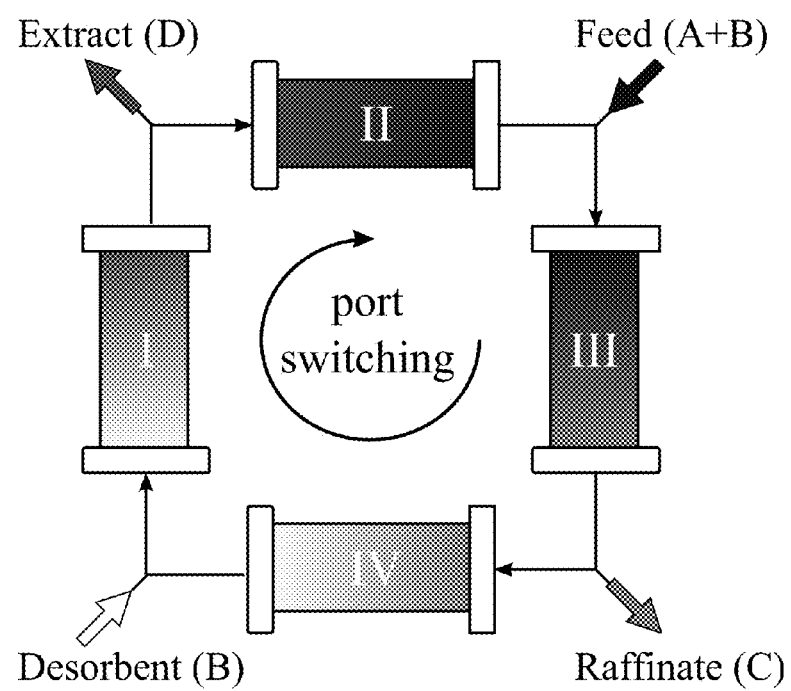
FIG. 1 illustrates an example of an SMBR unit suitable for the process of the present disclosure.

The process of using a SMBR takes advantage of continuous and counter-current movement of the liquid and stationary phases without actual movement of the solid. As shown in FIG. 1, the SMBR unit consists of multiple chromatographic columns that are interconnected in a cyclic conformation. A first reactant (e.g., "A") and a second reactant (e.g., "B") can be supplied to the SMBR at each step of a sequential repeating injection cycle, where the SMBR includes zones, as discussed herein, each having an injection point and each containing a solid separation media. One of either the first reactant or the second reactant can be used as the desorbent in the SMBR process. Both the reactants and the desorbent are supplied continuously during which time an extract stream and a raffinate stream are withdrawn through outlet ports from the SMBR. In one embodiment, the first reactant and the second reactant react in the SMBR during the sequential repeating injection cycle to form a first product (e.g., "C"). The solid separation media in addition to helping to separate the reactants and product can also act as a catalyst for the reaction of the first reactant and the second reactant. The first product can either move quickly through the chromatographic columns of the SMBR such that it is recovered from the raffinate stream of the SMBR, or it can be recovered through the extract stream of the SMBR.

In another embodiment, a first reactant (e.g., "D") and a second reactant (e.g., "E") react in the SMBR during the sequential repeating injection cycle to form a first product (e.g., "F") and a second product (e.g., "G"). The solid separation media in addition to helping to separate the reactants and product can also act as a catalyst for the reaction of the first reactant and the second reactant. One of either the first product or the second product will move more quickly through the chromatographic columns of the SMBR such that it is recovered from the raffinate stream of the SMBR while the other product (the more strongly retained component) will be recovered through the extract stream of the SMBR.

The SMBR includes injection points (a first injection point for the first reactant and the second reactant and a second injection point for the desorbent inlet for one of either the first reactant or the second reactant) and outlet points (an extract stream and a raffinate stream) that divide the SMBR into four zones. Each zone is allowed to have a different velocity and hence there are four control parameters. The counter-current motion of the liquid and adsorbent phases is achieved by switching both injection points and the outlet points simultaneously at a regular interval in the direction of liquid flow. Each of these regular intervals is a step that goes into one sequential repeating injection cycle of the SMBR. This switching time of the ports is also a control parameter.

So, the SMBR provides for a continuous and counter-current operation that combines chemical reaction and separation within one single apparatus. The SMBR unit employs multiple fixed-bed columns (or sections of columns), where each fixed bed column contains separation media to separate the reaction product(s) and can contain a catalyst for the reaction. Different reactions may require different number and configurations of the multiple fixed-bed columns. For example, from 4 to 24 fixed-bed columns can be used in forming a SMBR. The principal inputs and outputs of the SMBR are the feed, the extract, and the raffinate, where each fixed-bed column includes an injection point and an outlet point. Each stream flows into or out of the fixed-bed column of the SMBR at individual locations and at a particular flow rate which is independently controlled.

During the process, the SMBR switches the injection points and the outlet points of liquids from one column to another (or between column sections) to approach the theoretical performance of a true countercurrent solid-liquid flow. Switching the injection points and the outlet points from one column to another can be accomplished using valves (e.g., rotary valves or a network of two-position or multi-position valves) which work in conjunction with the inlet and outlet lines of the multiple fixed-bed columns. The fluid-directing device accomplishes moving the locations of the input and output streams by directing the streams to the appropriate injection points or outlet points of the multiple fixed-bed columns. The liquid flow rates of the feed streams and the step times for the valves of the SMBR are controlled so that the slow and fast eluting reaction products (when a first product and a second product are formed) move in opposite directions relative to the movement or switching of inlet and outlet ports.

By way of example, the fixed-bed columns of the SMBR can be configured to provide four zones to provide for the reaction and to separate the reaction product(s) from the mixture into two fractions: the extract, which includes the slow-eluting fraction, and the raffinate, which includes the fast-eluting fraction. The four zones of the SMBR each perform a different function. Zone I contains fixed-bed columns between the desorbent inlet and the extract stream; Zone II contains fixed-bed columns between the extract stream and the feed inlet; Zone III contains fixed-bed columns between the feed inlet and the raffinate stream; and Zone IV contains fixed-bed columns between the raffinate stream and the desorbent inlet. Within the SMBR, Zones II and III serve to allow the fast and slow components to move farther apart, while Zones I and IV serve to prevent the slow components from falling too far back and the fast components from moving too far forward, respectively.

As discussed herein, the fixed-bed columns of the SMBR can include a catalyst for the reaction and separation media to separate the reaction product(s). The catalyst and the separation media can be provided on one structure or can be provided on separate structures in the fixed-bed columns of the SMBR. The separation media used in the fixed-bed columns of the SMBR can be selected so that the reaction components are less strongly adsorbed, while the reaction co-product(s) is more strongly adsorbed, thereby carrying them counter-currently with the simulated movement of the solids. So, for example, using strong acid cation exchange resins allows for less polar reaction components to be removed from the SMBR in the raffinate stream, while more polar reaction components to be removed from the SMBR in the extract stream.

The process of the present disclosure can use many different types of catalysts and separation media to carry out the reactions and separation. It can use either a single solid that can act as both catalyst and separation media, a combination of one or more solid catalysts and separation media, or a homogeneous catalyst with one or more separation media. The separation media can be conventional materials used in adsorption-type processes, including but are not limited to, polymeric resins, silica, alumina, molecular sieves, activated carbon or other known separation media that can separate the reaction product(s). The preferred solids are those that can function as both catalyst and separation media in a single solid. Examples of such solids include, but are not limited to, sulfonated ion exchange resin such as Amberlyst™ 15, Amberlyst™ 70, DOWEX™ MONOSPHERE™ M-31, or other commercially available strong acid polymeric resins.

Different reactions and separations of product(s) may require different catalyst and separation media combinations and/or different volume ratios of catalyst to separation media. For example, the catalyst and the separation media can be present in the SMBR in a volume ratio (catalyst: separation media) that ranges from 1:100 to 100:1. The catalyst and the separation media can also be present in the SMBR in a variety of configurations. For example, when present as separate structures the catalyst and the separation media can be present as a homogeneous mixture throughout the fixed-bed columns of the SMBR. Alternatively, the catalyst and the separation media can be present in alternating layers of catalyst and separation media along the fixed-bed columns of the SMBR. The thicknesses and relative positions of the layers can depend upon the reaction and the product(s) that need to be separated.

The SMBR can allow for the simultaneous purification of a product that is produced within the same unit operation. For example, consider the following equilibrium-limited reaction which generates the first product ("C") from the first and second reactants ("A" and "B"):

$$A+B \leftrightarrow C$$

In reactive separation processes, such as those that can occur in the SMBR, the first product "C" can be purified and removed while the reaction proceeds on a continuous basis. Thus it is possible for the overall conversion to exceed the equilibrium limit.

In an additional example, consider the following equilibrium-limited reaction which generates a first product ("F") and a second product ("G") from a first reactant ("D") and a second reactant ("E"):

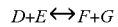
$$D+E \leftrightarrow F+G$$

In reactive separation processes, such as those that can occur in the SMBR, the first product "F" and/or the second product "G" can be purified and removed while the reaction proceeds on a continuous basis. Thus it is possible for the overall conversion to exceed the equilibrium limit. It is appreciated that the process of the present disclosure can be used for other equilibrium limited reactions that use more than two reactants and/or produce three or more products.

In a conventional SMBR operating strategy the amount of each of the reactants (e.g., the inlet feed concentration) is fixed during each step of the sequential repeating injection cycle. So, for example, the feed concentration of the reactants is constant throughout the operation of the SMBR. In contrast to a constant amount of reactants being use, the process of the present disclosure allows for the amount of one or both of the first reactant and the second reactant injected at one or more of the injection points of the SMBR to be changed during one or more steps of the sequential repeating injection cycle. In other words, the amount of one or more of the reactants is allowed to be time-varying, which increases the productivity significantly. For example, the amount of one or both of the first reactant and/or the second reactant can be changed at a step of the sequential repeating injection cycle. As discussed herein, each step of the sequential repeating injection cycle has a predetermined time ($t_{step}$), and changing the amount of one or both of the first reactant and the second reactant can begin once a first percentage of $t_{step}$ is reached. For example, the first percentage of $t_{step}$ can be from 50 percent (%) to less than 100% of $t_{step}$. In an additional example, the first percentage of $t_{step}$ can be from 10% to 90% of $t_{step}$. In addition, the first percentage of $t_{step}$ can be from 65% to 67% of $t_{step}$. As these values will be highly case dependent other values are possible.

Figure 2:
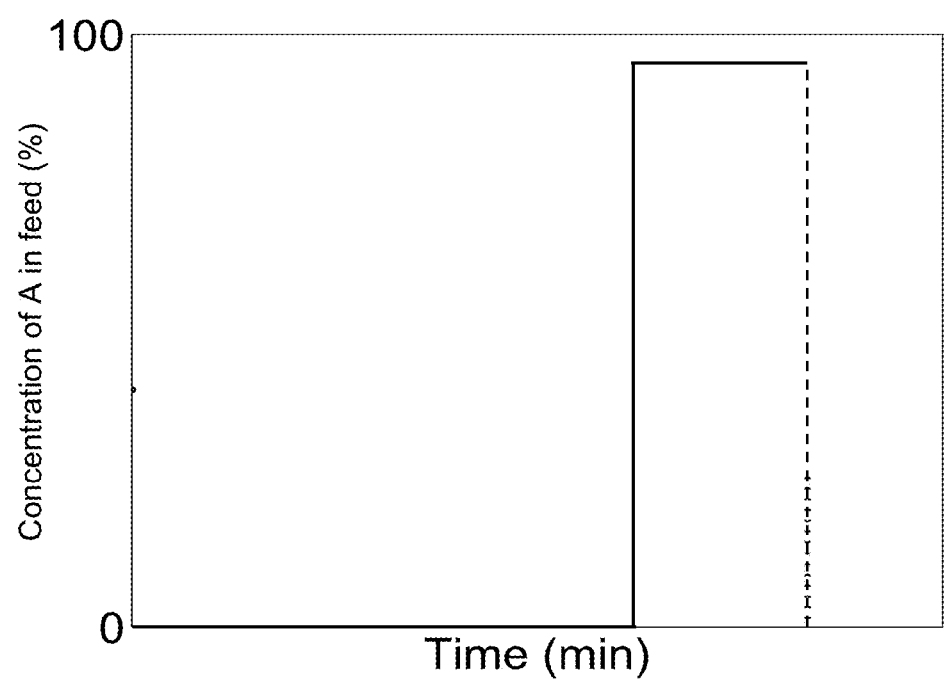
FIG. 2 illustrates an example of changing the feed composition once during a single step of a sequential repeating injection cycle according to one embodiment of the present disclosure.
Figure 3:
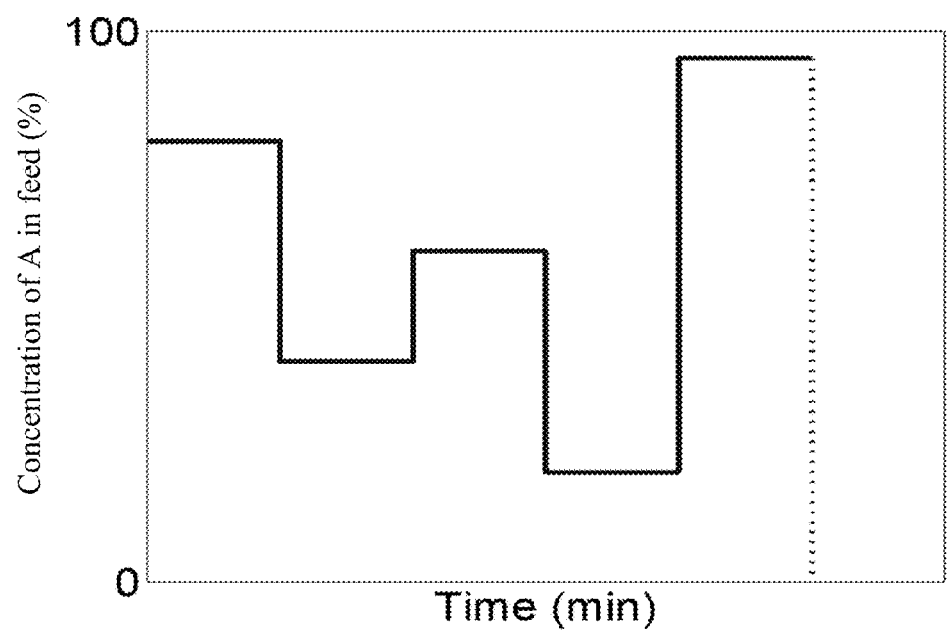
FIG. 3 illustrates an example of changing the feed composition two or more times during a single step of a sequential repeating injection cycle according to one embodiment of the present disclosure.

For the process of the present disclosure, changing the amount of one or both of the first reactant and/or the second reactant can be done once during a step of the sequential repeating injection cycle. For example, FIG. 2 provides an illustration of changing the amount of the first reactant during a step of the sequential repeating injection cycle, where pure desorbent (e.g., the second reactant) is fed to the SMBR at a first part of the step while the first reactant is fed at high concentration in a second part of the step. In an additional embodiment, changing the amount of one or both of the first reactant and/or the second reactant can be done at two or more times during a step of the sequential repeating injection cycle. FIG. 3 provides an illustration of this strategy. These modulations of the amount of the reactants may help to improve the process performance by overcoming the separation limitation of the internal concentration profiles inside the SMBR.

For the process, changing the amount of one or both of the first reactant and the second reactant can be done as a step change during the step. Alternatively, changing the amount of one or both of the first reactant and the second reactant can be done as a linear change during the step. It is also possible to use a combination of step and linear changes during the step. Other functions can also be used in changing the amount of the first reactant and/or the second reactant injected into the SMBR during a step of the sequential repeating injection cycle.

For the various embodiments, an example of changing the amount includes changing an inlet concentration (e.g., mole/volume) of one or more of the first reactant and the second reactant injected at one or more of the injection points of the SMBR during a step of the sequential repeating injection cycle. It is appreciated that changing the amount during a step of the sequential repeating injection cycle can be accomplished by changing the flow rate (e.g., volume/time) for one or both of the first reactant and the second reactant injected at one or more of the injection points of the SMBR.

As illustrated in FIGS. 2 and 3, the amount of the first reactant relative a total amount of the first reactant and the second reactant injected at one or more of the injection points of the SMBR can have different values. For example, the amount (e.g., weight percent or concentration) of the first reactant can have a first value relative a total amount of the first reactant and the second reactant injected at a given injection point of the SMBR during at least a first portion of a step of the sequential repeating injection cycle, and then change to a second value at a second portion of the step of the sequential repeating injection cycle (e.g., FIG. 2). As illustrated in FIG. 2, during a first portion of the step the amount of the first reactant can be zero (0) relative a total amount of the first reactant and the second reactant injected at a given injection point, and then at a second portion of the step the amount of the first reactant can change to a value greater than zero relative a total amount of the first reactant and the second reactant injected at a given injection point. Such values can range from zero to 100 percent (e.g., from zero to 75 percent). So, for example, the amount of the first reactant can be 100% relative the total amount of the first reactant and the second reactant injected at one or more of the injection points of the SMBR during a different portion of a step of the sequential repeating injection cycle.

The process can also include supplying the first reactant to the SMBR at a stoichiometric excess sufficiently large relative the second reactant that the first reactant acts as a desorbent for both a raffinate stream and an extract stream of the SMBR. When the first reactant is at a stoichiometric excess relative the second reactant (e.g., the second reactant in a stoichiometric deficit relative to the first reactant), the second reactant can react to extinction in the SMBR. Suitable examples of supplying the first reactant in the stoichiometric excess relative to the second reactant for the reaction include supplying a stoichiometric ratio of the second reactant to the first reactant in a range from 1:1.1 to 1:10; in a range from 1:1.5 to 1:5; or in a range from 1:2 to 1:3.

The SMBR can be operated at a pressure and a predetermined temperature suitable for the reaction. Operating conditions will depend upon the catalyst and the separation media used in the SMBR. Predetermined temperatures for the reactions in the SMBR can be from 0° C. to 200° C. Typical operating pressures for the reactions in the SMBR can be from 101 KPa to 2000 KPa. As appreciated by one skilled in the art, other predetermined temperatures and pressures are possible depending upon the reaction. The operating conditions can be set so that the streams of the reactants are in the liquid phase, and all components are in the liquid phase.

The process of the present disclosure can also include portions of either the raffinate stream and/or the extract stream being returned to the SMBR for further use (e.g., recycled back to the one or more zones of the SMBR). So the process can include supplying a portion of at least one of the raffinate steam and/or the extract stream to at least one of the zones of the SMBR. For example, one or both of the raffinate stream and the extract stream can undergo a separation process to produce two or more fractions. One or more of these fractions, depending upon its content, can be returned to the SMBR (e.g., to a location within the SMBR where the molar compositions of one or both of the first reactant and/or the second reactant have similar molar concentrations), while one or more of the other fractions can be collected as a product or as waste.

EXAMPLES

The following examples consider the production of propylene glycol methyl ether acetate ((DOWANOL™ PMA glycol ether acetate, The Dow Chemical Company, hereinafter "PMA") through the esterification of 1-methoxy-2-propanol (DOWANOL™ PM glycol ether, The Dow Chemical Company, hereinafter "PM") and the acetic acid (hereinafter "AA"). The esterification reaction is catalyzed by AMBERLYST™ 15 (The Dow Chemical Company), a cation exchange resin that functions both as a catalyst and an adsorbent. For the following Examples a multi-objective optimization problem is formulated to find a reactive separation strategy for the production of the PMA product.

The mathematical models provided herein are discussed in Agrawal, G.; Oh, J.; Sreedhar, B.; Tie, S.; Donaldson, M. E.; Frank, T. C.; Schultz, A. K.; Bommarius, A. S.; Kawajiri, Y., Optimization of reactive simulated moving bed systems with modulation of feed concentration for production of glycol ether ester. Journal of chromatography A 2014, 1360, 196-208, which is incorporated herein in its entirety. A transport dispersive model with a linear driving force for the adsorption rate is used for modeling the SMBR, and the adsorption equilibrium and kinetics parameters are estimated from the batch and single column injection experiments by using the inverse method. To design a SMBR process, a multi-objective optimization problem is formulated. The multiple objectives are to maximize the production rate of DOWANOL™ PMA glycol ether acetate and the conversion of the esterification reaction. A conventional SMBR operating strategy has been optimized and further extended to the process of the present disclosure, which is based on changes in the amounts of reactants fed to the SMBR during steps of the sequential repeating injection cycle.

The SMBR unit, as shown in FIG. 1, consists of multiple chromatographic columns that are interconnected in a cyclic conformation. The feed is a mixture of AA and PM while the desorbent consists of PM. The AA reacts with PM under acid-catalyzed conditions forming PMA and water. As this esterification proceeds inside the SMBR, both PMA and water are continuously removed thus shifting the equilibrium in the forward direction. Since PMA is the faster-moving component, it is recovered from the raffinate stream while the strongly retained component, water, is recovered through the extract steam.

The SMBR unit shown in FIG. 1 includes two inlet streams for the reactants and the desorbent, and two outlet streams for the extract stream and the raffinate stream. These inlet and outlet streams divide the entire SMBR into four zones. Each zone can be controlled independently hence there are four degrees of freedom; reactant, desorbent, extract and one of the zones velocity. The zone velocities are in general selected such that Zone II and III become the reaction plus separation Zones while Zone I and IV regenerates the columns. Further, the counter-current motion of the solid phase is simulated by switching both inlet and outlet ports simultaneously in the direction of liquid flow. The two consecutive switching of the ports defines a step and the time for which this step lasts is also a degree of freedom. Four such steps complete a sequential repeating injection cycle and the SMBR system comes back to its original configuration. This cyclic operation of SMBR is constantly repeated to extract pure PMA and water from the raffinate and extract streams. The total number of degrees of freedom that affect the performance of SMBR are five. However, there could also be some extra degrees of freedom depending on the SMBR operating strategy that is being implemented.

For example, for a constant feed concentration the feed concentration is kept constant during the entire step. The feed composition i.e. percentage of AA and PM is however optimized during the SMBR optimization. Hence, the number of degrees of freedom that affect the performance of SMBR in this operating strategy is six; the feed composition, switching time, and the velocities of the desorbent, feed, extract, and Zone I. It has been found that there exists the optimal feed concentration that is not necessarily 100%. A too high feed concentration would achieve low conversion, since the feed cannot be mixed with the desorbent effectively. The present disclosure, in contrast, finds the optimal feed concentration using the model and nonlinear optimization.

The productivity and specific strategy for the present disclosure allows for the feed concentration to be manipulated in a time-varying manner so that the feed concentration has a sharp local peak, which is located away from the raffinate and extract streams. Such a local increase of the feed mixture may allow higher purity and recovery for the same productivity and solvent consumption. The examples provided herein look at an operation where the feed concentration is changed only once in a step, as shown in FIG. 2. The time interval at which the inlet feed concentration changes is an extra degree of freedom. Hence, the degrees of freedom that affect the performance of SMBR in this operating strategy is eight; the two feed compositions in two different time intervals, intermediate time $t_i$, desorbent velocity, switching time, feed, extract and the velocity of Zone I. Embodiments of the present process may be more promising in terms of improving the PMA production rate compared to the standard SMBR operation because of its greater flexibility. The modulation of inlet feed concentration may improve the process performance by overcoming the separation limitation of the internal concentration profiles inside the SMBR. Such a process can be implemented using two pumps in parallel or by using a gradient based feed pump.

The examples of the present disclosure utilize a transport dispersive model with a linear driving force for the adsorption rate to model the SMBR. Here, the axial dispersion phenomenon and diffusion into the adsorbent particles inside the columns are accounted separately using an overall axial dispersion coefficient and individual mass transfer coefficients for each component. The mass balance equations in the liquid and solid phases for component i in the jth adsorption column are written as follows.

Mass balance in the liquid phase:

$$\frac{\partial C_i^j(x,t)}{\partial t} + \frac{1-\epsilon_b}{\epsilon_b} K_{m,i}(q_i^{j,eq}(x,t) - q_i^j(x,t)) + u^j(t)\frac{\partial C_i^j(x,t)}{\partial x} = D_{ax}\frac{\partial^2 C}{\partial x^2}. \quad (1)$$

where $C_i^j(x,t)$, and $q_i^j(x,t)$ are the concentration in the liquid and the solid phase at axial distance x and time t, respectively, $q_i^{j,eq}(x,t)$ is the concentration in the solid phase that is in equilibrium with the liquid phase, Eb is the bed porosity, Km,i is the solid phase based mass transfer coefficient of the ith component, Dax is the axial dispersion coefficient, $u^j(t)$ is the super-critical velocity of the column, x is the axial distance and t is the time. The subscript i represents the component index while superscript j refers to the jth column. Mass balance in the solid phase is:

$$\frac{\partial q_i^j(x,t)}{\partial t} = K_{m,i}(q_i^{j,eq}(x,t) - q_i^j(x,t)) + v_i r^j(x,t). \quad (2)$$

where Vi is the stoichiometric reaction coefficient of the ith component and $r^j(x,t)$ is the net reaction rate in the jth column at distance x and time t. The equilibrium between solid and liquid phases is represented by the following linear adsorption isotherm equation:

$$q_i^{j,eq}(x,t) = H_i C_i^j(x,t). \quad (3)$$

where Hi is the Henry constant. The reaction rate of esterification reaction is assume to be given as a second order model:

$$r^j(x,t) = k_1\left(q_{AA}^j(x,t)q_{PM}^j(x,t) - \frac{1}{K_{eq}}q_{PMA}^j(x,t)q_{Water}^j(x,t)\right). \quad (4)$$

where $k_1$ is the forward reaction rate constant while Keq is the equilibrium constant of the esterification reaction. The subscripts AA, PM, PMA and water refer to the acetic acid, PM, PMA and Water component, respectively. It has to be noted that the reaction is assumed only in the solid phase, and hence equation (4) represents a heterogeneous catalyzed reaction.

The boundary conditions are given as follows:

Mass balance between jth and (j+1)th column is:

$$C_i^{j+1}(0,t)u^{j+1}(t) = C_i^j(L,t)(u^j(t) - u_{Ex}^j(t) - u_R^j(t)) + C_{i,F}u_F^{j+1}(t) + C_{i,D}u_D^{j+1}(t) + D_{ax}\frac{\partial C_i^j(x,t)}{\partial x}\bigg|_{x=0}. \quad (5)$$

where $u_R^j$, $u_{Ex}^j$, $u_D^j$ and $u_F^j$ are the velocities of raffinate, extract, desorbent and the inlet feed stream, respectively. These values are positive only if raffinate, extract, desorbent, or feed is withdrawn or fed, and zero otherwise. The symbol $C_{i,F}$ and $C_{i,D}$ are the concentrations of ith component in the feed and desorbent, respectively and L is the length of the column. The other boundary condition determines the concentration at the outlet of column.

$$\left.\frac{\partial C_i^j(x,t)}{\partial x}\right|_{x=L} = 0. \quad (6)$$

The flow balance at the inlet and outlet ports should also be satisfied to maintain the consistency of the flow. Hence, the following equations are written.

$$u^{j+1}(t) = u^j(t) - (u_R^j(t) + u_{Ex}^j(t) + u_F^j(t)) + (u_D^{j+1}(t) + u_F^{j+1}(t)). \quad (7)$$

$$i=1, \ldots, N_{comp}, j=1, \ldots, N_{column}-1$$

where the symbol $N_{comp}$ refers to the total number of components and $N_{column}$ is the total number of columns. In SMBR, the counter-current movement of the solid phase is simulated by discrete shifting of inlet and outlet ports. As a result, the SMBR systems arrives at a cyclic steady state (CSS). At the CSS, the concentration profiles still change inside the columns however, the snapshots of internal concentration profiles at the beginning and at the end of the step are identical except that they are shifted by the length of one column. Since SMBR is a symmetric operation i.e. all the steps are identical except the shifting of inlet and outlet streams due to valve switching, a single step formulation is used to write the CSS. In this formulation, the concentration profiles at the beginning of the step in the jth column are identical to the concentration profiles at the end of the step in the (j+1)th column. The formulation is written as:

$$C_i^j(x,0) = C_i^{j+1}(x,t_{step}), \; i=1,\ldots,N_{comp}, \; j=1,\ldots, N_{column}-1 \quad (8)$$

$$q_i^j(x,0) = q_i^{j+1}(x,t_{step}), \; i=1,\ldots,N_{comp}, \; j=1,\ldots, N_{column}-1 \quad (9)$$

$$C_i^{N_{column}}(x,0) = C_i^1(x,t_{step}), \; i=1,\ldots,N_{comp} \quad (10)$$

$$q_i^{N_{column}}(x,0) = q_i^1(x,t_{step}), \; i=1,\ldots,N_{comp} \quad (11)$$

where $t_{step}$ is the step time.

A multi-objective optimization problem is formulated to find a preferred design of the SMBR. The multiple objectives are to maximize the production rate of PMA in the raffinate stream and the conversion of esterification reaction. In addition, the amount of water in the raffinate stream is minimized because water can form azeotropes with PMA in the downstream processing. Hence, the water purity in the raffinate stream is enforced to be less than 1.0 wt %. Similarly, it is also desired to maximize the PMA recovered in the raffinate stream. Therefore, the PMA recovery from the raffinate stream is enforced to be more than 90 wt. %.

Given these parameters, the overall problem is as follows:

Maximizing PMA production rate (g/hr):

$$\max Pr = \frac{A_{cs} MW_{PMA}}{t_{step}} \sum_{j=1}^{N_{Column}} \int_0^{t_{step}} C_{PMA,R}^j(L,t) u_R^j(t) dt, \quad (12)$$

Maximizing conversion of acetic acid:

$$\max Co = \quad (13)$$

$$1 - \frac{\sum_{j=1}^{N_{Column}} \int_0^{t_{step}} (C_{AA,R}^j(L,t) u_R^j(t) + C_{AA,Ex}^j(L,t) u_{Ex}^j(t)) dt}{\sum_{j=1}^{N_{Column}} \int_0^{t_{step}} C_{AA,F} u_F^j(t) dt},$$

subject to equations (1)-(11), water purity in the raffinate stream outlet (wt %):

$$Pur_{Water} = \frac{\sum_{j=1}^{N_{Column}} \int_0^{t_{step}} MW_{Water} u_R^j(t) C_{Water,R}^j(L,t) dt}{\sum_{j=1}^{N_{Comp}} \sum_{j=1}^{N_{Column}} \int_0^{t_{step}} MW_i u_R^j(t) C_{i,R}^j(t) dt} \leq 1\%, \quad (14)$$

PMA recovery in the raffinate stream outlet:

$$Rec_{PMA} = \quad (15)$$

$$\frac{\sum_{j=1}^{N_{Column}} \int_0^{t_{step}} u_R^j(t) C_{PMA,R}^j(L,t) dt}{\sum_{j=1}^{N_{Column}} \int_0^{t_{step}} (u_R^j(t) C_{PMA,R}^j(L,t) + u_{Ex}^j(t) C_{PMA,Ex}^j(L,t)) dt} \geq 90\%.$$

Bounds on the zone flow rates:

$$u_L \leq u^j(t) \leq u_U. \quad (16)$$

where $P_r$ and $C_o$ are the objective functions, $A_{cs}$ is the area of cross-section of the column and $MW_i$, is the weight average molecular weight of ith component and $C_{i,R}$ and $C_{i,Ex}$ are the concentrations of ith component in the raffinate and extract stream, respectively. In addition, a lower bound and an upper bound are introduced on the zone velocities because of the restriction of maximum pressure drop that can be experienced by the pumps in the SMBR system. The symbols $u_L$ and $u_U$ refers to the lower and upper bounds and their corresponding values are set at 0 m/h and 10 m/h, respectively. This multi-objective problem is converted into a single-objective problem by using the epsilon-constrained method where the conversion of acetic acid (AA) is imposed as a constraint.

$$Co \geq \epsilon \quad (17)$$

Figure 4:
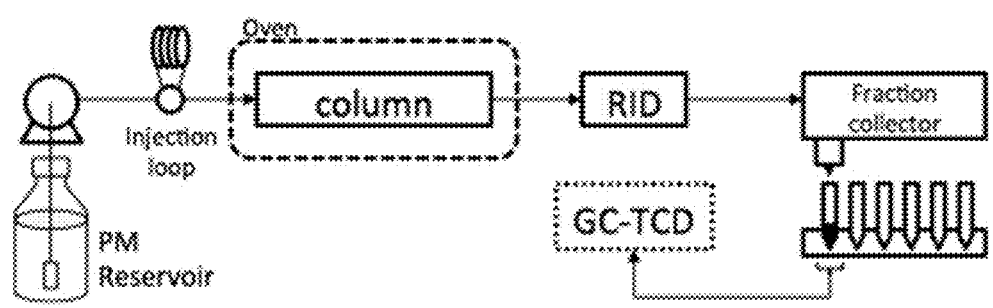
FIG. 4 is a schematic of a single column pulse-injection experiment.

To obtain parameters in the mathematical model, laboratory experiments were carried out as discussed in Agrawal, G.; Oh, J.; Sreedhar, B.; Tie, S.; Donaldson, M. E.; Frank, T. C.; Schultz, A. K.; Bommarius, A. S.; Kawajiri, Y., Optimization of reactive simulated moving bed systems with modulation of feed concentration for production of glycol ether ester. Journal of chromatography A 2014, 1360, 196-208. The schematic of a single column pulse-injection experiment is shown in FIG. 4. The single column pulse-injection system shown in FIG. 4 includes a stainless steel column of an internal diameter of 0.8 cm and the height of 25 cm. The Amberlyst 15 cation exchange resin was swollen by keeping it in AA and later used for packing the column using the slurry technique. A pulse of AA and PM mixture is injected in the column by using RH-7725i valve from Rheodyne and pure PM was used as the desorbent. The PM was dehydrated using 3 Å molecular sieves before feeding into the system. The outlet of the column was then fractionated using a fraction collector (Shimadzu, FRC-10a) and analyzed for measuring the concentrations of AA, PM, PMA and water using Gas Chromatography (GC) with the TCD detector. The TCD detector measured the water concentration accurately below 5 vol %. All the tubing that connected various parts of the instrument was of 0.16 cm (1/16 inch) outer diameter and the total extra column volume was 0.343 ml. Experimental details are provided in Table 1.

The column porosity was estimated by injecting Dextran (Dextran 25000, Spectrum) as a tracer. Dextran is a high molecular weight substance that is unable to penetrate in the pores of Amberlyst 15. Since Dextran is not soluble in PM, the column was first saturated with water and then Dextran dissolved in water was injected into the system. The bed porosity was calculated to be 0.31 after subtracting the extra column volume from the retention time of Dextran.

The following explains the methodology used for estimating the adsorption equilibrium, axial dispersion coefficient and kinetic parameters of the SMBR model. These model parameters are estimated by fitting the model to the multiple pulse-injection experiments (performed over a single column) simultaneously, and is discussed in Agrawal, G.; Oh, J.; Sreedhar, B.; Tie, S.; Donaldson, M. E.; Frank, T. C.; Schultz, A. K.; Bommarius, A. S.; Kawajiri, Y., Optimization of reactive simulated moving bed systems with modulation of feed concentration for production of glycol ether ester. Journal of chromatography A 2014, 1360, 196-208.

TABLE 1

Experimental details

| Parameter | Value |
| --- | --- |
| Column details | |
| Length (L) | 25 cm |
| Diameter (D) | 0.8 cm |
| Bed porosity ($e_b$) | 0.31$^a$ |
| Mobile phase | PM |
| Stationary phase | |
| Resin | Amberlyst 15 |
| Particle size | <707 μm |
| Swelling ratios of Amberlyst 15 (compared to dry resin) | |
| PM | 1.5 |
| Water | 1.55 |
| Dead volume | 0.343 ml |

Fitting Model to the Pulse-Injection Experiments

The inverse method approach is used to estimate the model parameters due to its experimental simplicity. In the inverse method approach, the simulated concentration profiles of the pulse-injection experiments are fitted to the experimental chromatograms to estimate the reliable set of model parameters. A least-square technique is used that minimizes the sum of the squares of the difference between the concentrations predicted by the model and the experimental observations. The objective function, $\Phi$, is formulated as:

$$\Phi = \min_{H_i, K_{m,i}, D_{ax}, k_1, K_{eq}, e_b} \sum_{k=0}^{N_{exp}} \sum_{i=1}^{N_{Comp}} \sum_{l=1}^{N_{t,i}^k} (C_{i,l}^{k,mod} - C_{i,l}^{k,exp})^2 + \rho \sum_{m=1}^{N_{reg}} (\theta_{reg,m}^{model} - \theta_{reg,m}^{exp}). \quad (18)$$

where the subscript i and l refer to the components and the time points at which samples are collected while superscript k denotes the experimental index. The symbol $N_{exp}$ refers to the total number of experiments considered, $N_{comp}$ refers to the total number of components present in the system, $N_{t,i}^k$ refers to the total number of concentration data points considered for the ith component in the kth experiment, and $N_{reg}$ is the number of regularization parameters discussed below. In the objective function, the Tikhonov regularization terms were include to prevent significant deviation of parameter values which are estimated from separate experiments. The Tikhonov regularization is a standard approach to reduce the non-uniqueness of the estimated parameter set. The equilibrium constant $K_{eq}$ and bed porosity in $$\theta_{reg}^{model}; \text{ i.e. } \theta_{reg}^{model} = [K_{eq}, \epsilon]^T.$$

were also included. This is because in parameter estimation with the chromatograms, these parameters are found to be insensitive to the fitting. The coefficients of the regularization term, ρ, is found by the best compromise between the model fitting and the deviation of $e_b$ and $K_{eq}$ values from the desired ones. The resulting system of equations for the model fitting is solved in MATLAB by using the fmincon optimizer with the interior-point algorithm.

Figure 5A:
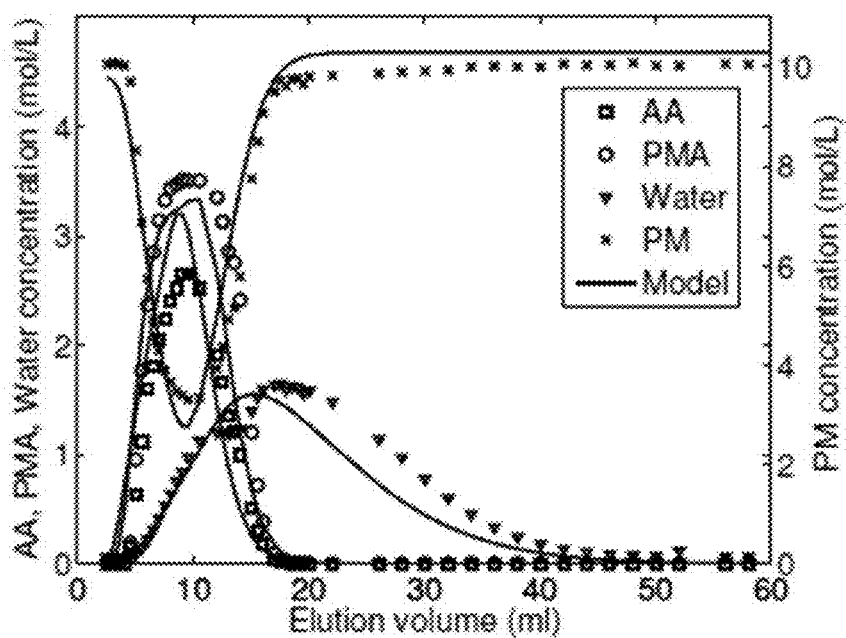
FIGS. 5(a) and 5(b) provide a comparison of the elution profiles described by the fitted model and the experimental chromatograms according to one embodiment of the present disclosure.
Figure 5B:
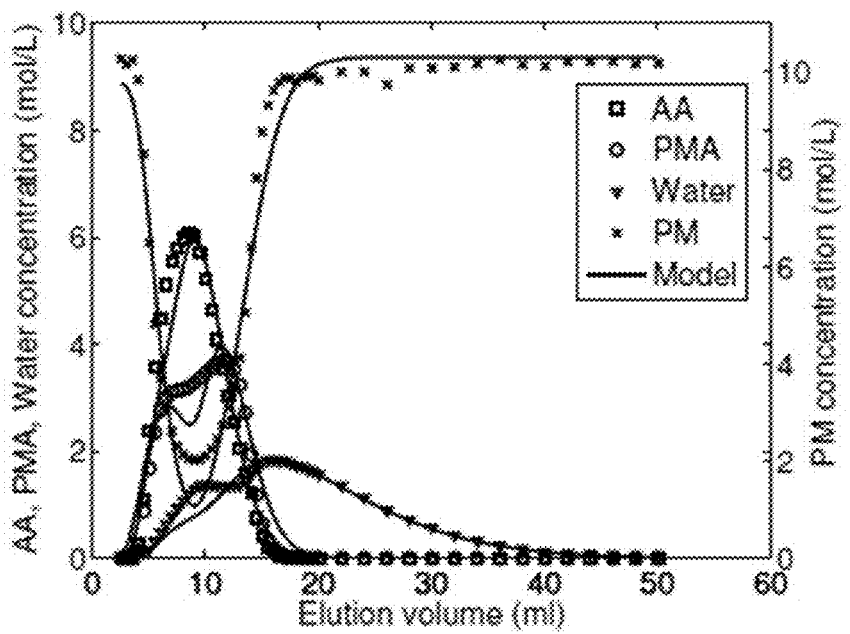

The model fitting results for the pulse-injection experiments are now discussed. There are in total 12 model parameters; four Henry constants, four mass transfer coefficients, two reaction parameters, an axial dispersion coefficient and the bed porosity. These parameters have been simultaneously estimated by fitting the single column model to two different pulse-injection experiments. The two pulse-injection experiments were performed by injecting a pulse of 50 vol % and 75 vol % AA concentration in PM at 110° C. with 5 ml injection loop and at 0.5 ml/min flow rate, respectively. The two experimental chromatograms were considered to increase the reliability of the estimated parameter set. FIGS. 5(a) and 5(b) show the comparison of the elution profiles described by the fitted model and the experimental chromatograms. The concentration profiles of AA, PMA and water are plotted on the left y-axis while PM concentration is shown on the right y-axis. The solid lines represent the predicted concentration profiles from the model and the markers represent the experimental data. As can be seen from the FIGS. 5(a) and 5(b), the model was able to fit the concentration profiles of all the components to a reasonable extent for both the experiments. The corresponding optimum model parameters are listed in Table 2.

TABLE 2

Optimized model parameters obtained by fitting the model to the pulse-injection experiments in FIG. 5.
Optimal model parameters

| $H_{AA}$ | $H_{PM}$ | $H_{PMA}$ | $H_{water}$ |
| --- | --- | --- | --- |
| 0.474 | 0.226 | 0.001 | 1.648 |
| $K_{m, AA}$ (min$^{-1}$) | $K_{m, PM}$ (min$^{-1}$) | $K_{m, PMA}$ (min$^{-1}$) | $K_{m, water}$ (min$^{-1}$) |
| 0.350 | 1.772 | 1.505 | 0.286 |
| $k_1$ (L/mol · min) | $K_{eq}$ | $D_{ax}$ (cm$^2$/min) | $e_b$ |
| 0.195 | 0.862 | 0.334 | 2.735 |

Figure 6:
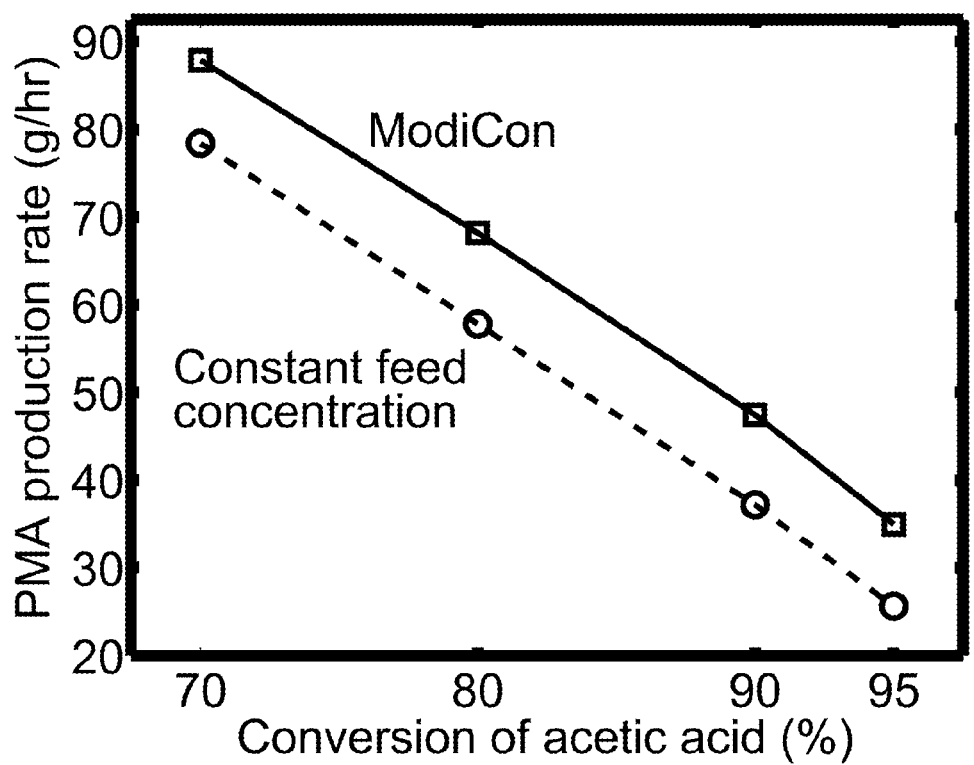
FIG. 6 provides a Pareto plot for both constant feed concentration and the process of changing the amount of reactants according to one embodiment of the present disclosure.

The Pareto plot for the multi-objective optimization problem is shown in FIG. 6 for both constant feed concentration and the process of changing the amount of reactants according to the present current disclosure. As can be seen from FIG. 6, the production rate of PMA through the raffinate stream decreases with increases in the conversion of AA. Thus the higher conversion of acetic acid is not favorable to high production rates of PMA, an observation that is discussed later while discussing the internal concentration profiles of the SMBR. Further, the process of the present disclosure shows consistent improvement over the constant feed concentration strategy for 70-90% conversion of AA. In addition, the improvement in the PMA production rate becomes more significant at a higher conversion of AA over the constant feed concentration strategy. Thus, the process of the present disclosure has significant potential to improve the process performance of the SMBR.

Figure 7A:
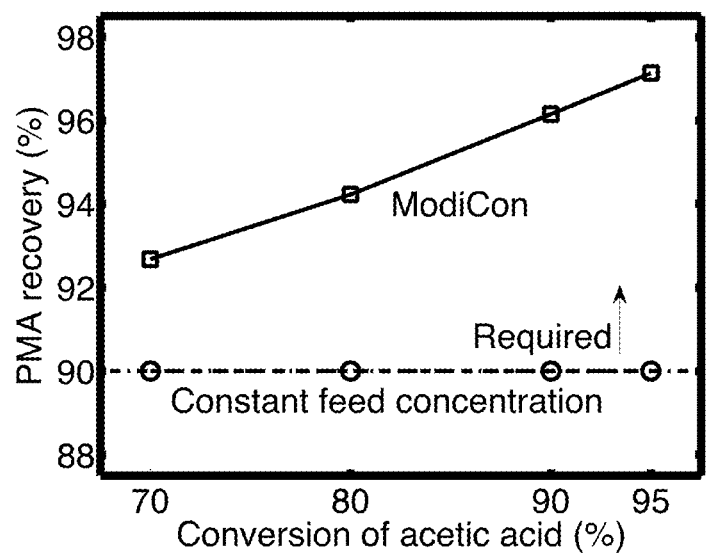
FIGS. 7(a) and 7(b) provide plots of optimum PMA recovery (7(a)) and water purity (7(b)) in the raffinate stream compared to the SMBR process specifications for both a constant feed concentration and a feed concentration according to one embodiment of the present disclosure.
Figure 7B:
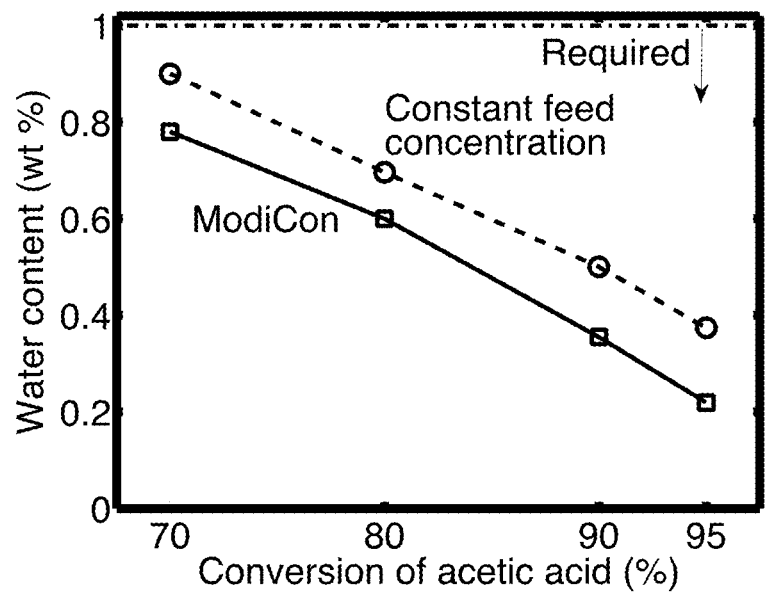

In addition to the Pareto plot, the amount of PMA recovered and the water purity (wt %) in the raffinate stream outlet are also compared with the required process specifications of the SMBR. As can be seen from FIG. 7(a), the PMA recovery was always an active constraint at the optimal solution for the constant feed concentration strategy. However, such is not the case with the process of the present disclosure. In the present disclosure, the PMA recovery obtained was higher than 90% and its value increased with increase in the conversion of AA. Thus, the process of the present disclosure is more advantageous to obtain high recovery of PMA through the raffinate stream. Water purity in the raffinate stream outlet is shown in FIG. 7(b), which does not become the bottleneck for achieving a high conversion. This constraint was not active for both of the operating strategies. Hence, the purity of water was always below 1 wt % thus fulfilling the required process specifications across the whole operating range. The amount of water in the raffinate stream outlet is important because of the azeotrope formation during the downstream distillation. Hence, the lower water content in the raffinate stream helps to ease the downstream separation. Since the process of the present disclosure leads to lower purity of water compared to the constant feed concentration strategy, it is also favorable for reducing the downstream cost.

Figure 8:
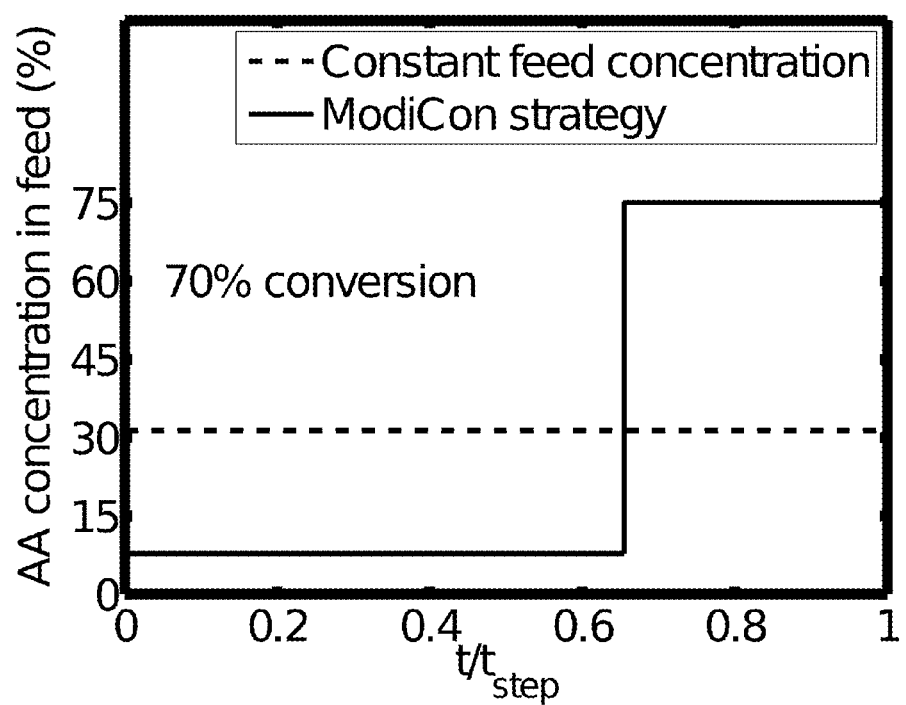
FIG. 8 provides an illustration of an inlet feed concentration profile within a single step for a 70% conversion of acetic acid according to one embodiment of the present disclosure.
Figure 9:
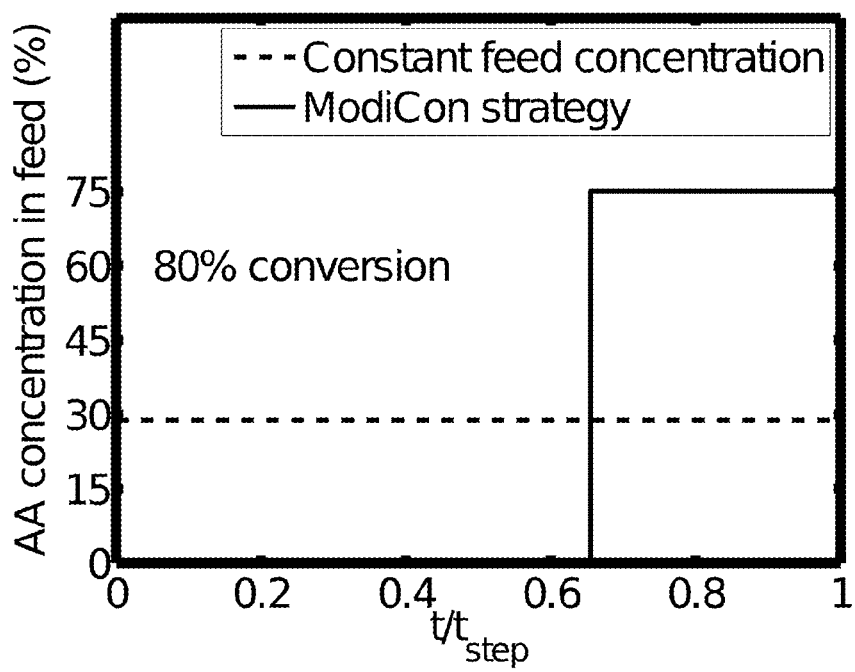
FIG. 9 provides an illustration of an inlet feed concentration profile within a single step for an 80% conversion of acetic acid according to one embodiment of the present disclosure.
Figure 10:
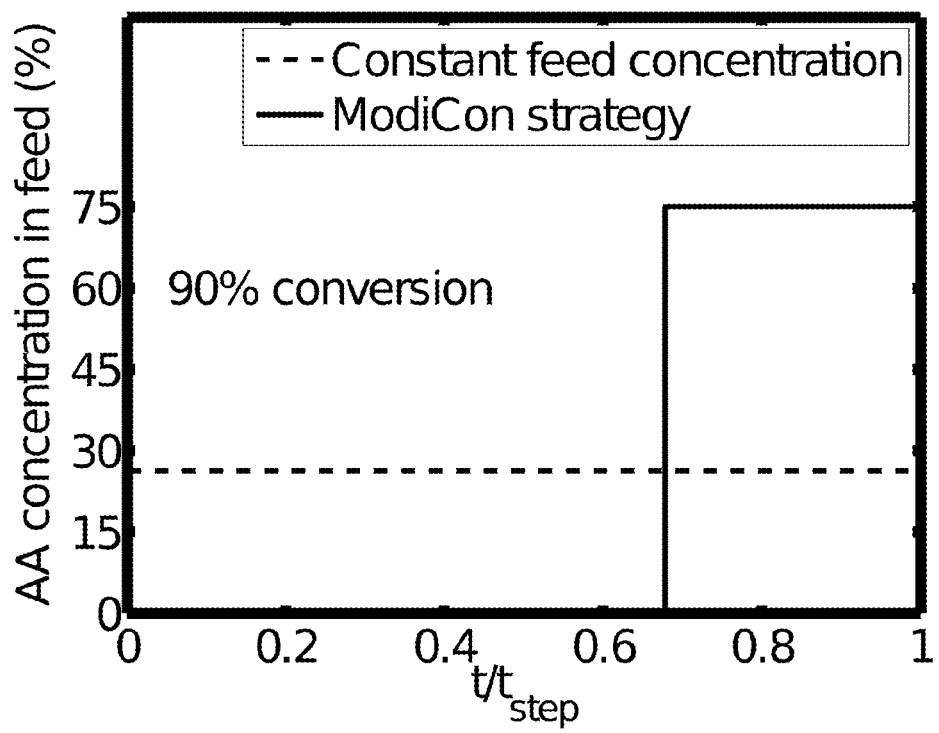
FIG. 10 provides an illustration of an inlet feed concentration profile within a single step for a 90% conversion of acetic acid according to one embodiment of the present disclosure.

Inlet feed concentration profiles obtained by both the operating strategies are now discussed, where the inlet feed composition was allowed to change between 0% and 75% of AA. The feed concentration profiles for a single step are shown in FIGS. 8, 9 and 10 for 70%, 80% and 90% conversion of AA, respectively. In addition, the feed concentrations values for both the operating strategies are also listed in Table 3.

TABLE 3

Optimized inlet feed concentration values for the constant feed concentration and the ModiCon strategy.

| Conversion of acetic acid (%) | Inlet feed concentration | |
|---|---|---|
| | Constant feed concentration strategy | ModiCon strategy |
| 70 | 31.5% AA for [0, $t_{step}$] | 7.85% AA for [0, 0.65 $t_{step}$] 100% AA for [0.65 $t_{step}$, $t_{step}$] |
| 80 | 28.8% AA for [0, $t_{step}$] | 0% AA for [0, 0.65 $t_{step}$] 100% AA for [0.65 $t_{step}$, $t_{step}$] |
| 90 | 26.3% AA for [0, $t_{step}$] | 0% AA for [0, 0.67 $t_{step}$] 100% AA for [0.67 $t_{step}$, $t_{step}$] |

It is to be noted that these feed concentration profiles are obtained at the cyclic steady state. Hence, the end of the previous step precedes the steps shown in FIGS. 8-10. As can be seen from Table 3, the feed concentration, in the constant feed concentration strategy, changes from 31.5% to 26.3% AA while increasing the conversion of AA from 70% to 90%. On the other hand, the process of the present disclosure is very similar in a variety of the scenarios. In the process of the present disclosure, either the pure PM or AA at low concentration is fed for the first 66% of the step time and then the feed composition is switched to 75% AA. These feed concentration profiles can be explained from the internal concentration profiles and the reaction rates inside the SMBR.

Figure 11A:
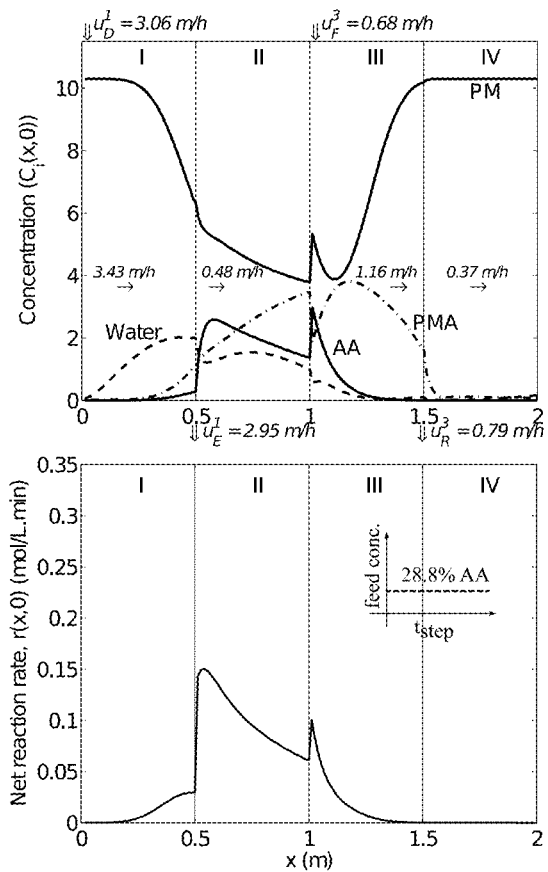
FIGS. 11(a) and 11(b) provides internal concentration profiles and net reaction rates inside an SMBR at the beginning of the step for both a constant feed concentration (FIG. 11(a)) and a feed concentration profile according to one embodiment of the present disclosure (FIG. 11(b)).
Figure 11B:
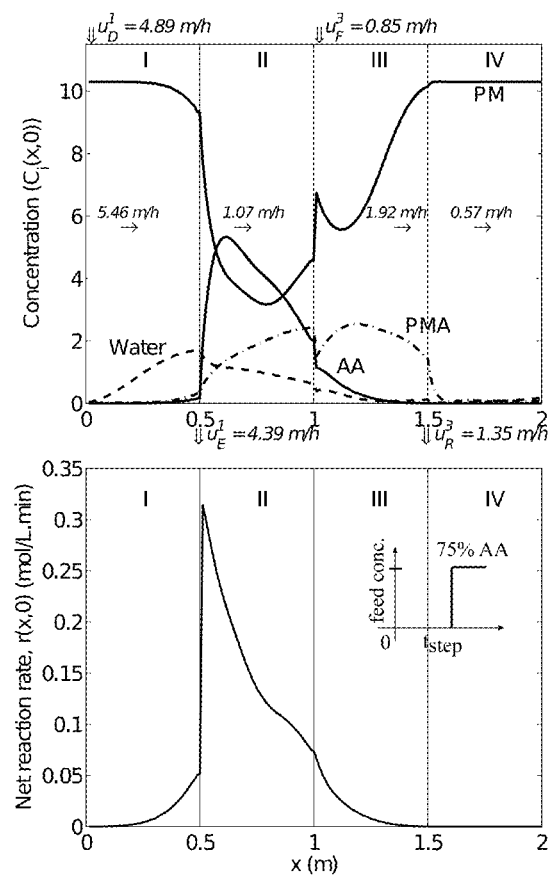

FIGS. 11(a) and 11(b) show the snapshot of internal concentration profiles and the net reaction rate $r^j(x,t)$ for the constant feed concentration (FIG. 11(a)) and the process of the present disclosure (FIG. 11(b)), respectively. As expected, in both operating strategies the net reaction rate inside the SMBR is the highest in Zone II, where the AA reacts with PM to form PMA and water. The strongly retained component water can be recovered from the extract stream while the faster moving component PMA is sent to Zone III, and finally recovered from the raffinate stream.

There are notable differences in the concentration profiles of these two different operating strategies. In particular, the concentration profile of AA is significantly different; in the process of the present disclosure, the concentration of AA has a significantly sharper peak in Zone II (FIG. 11(b)). This increase in the AA concentration in Zone II in the process of the present disclosure leads to a higher net reaction rate, while the net reaction rate in the constant feed concentration strategy has a relatively flat profile that spreads both in Zones II and III (FIG. 11(a)). The limited production rate of the constant feed concentration strategy can be explained by the reaction equilibrium in Zone II and III. If the feed was supplied at a faster flow rate, the net reaction rate in Zone III would increase, leading to formation of excess PMA. The excess PMA would move to Zone IV, and start the reverse reaction with a small amount of water that exists in this zone. This reverse reaction forms AA and PM, and the conversion would decrease. If the reaction rate in Zone III was even higher, a larger amount of PMA is formed, which would enter Zone I through the recycle line, and would lead to an even higher rate of reverse reaction.

On the other hand, the process of the present disclosure avoids a high net reaction rate in Zone III by the modulation of the feed concentration. As can be seen in FIGS. 8-10, at the beginning of a step, the concentration of AA in the feed is zero, which prevents an increase in the net reaction rate in Zone III. After all components moves downstream, the concentration of AA in the feed increases. This modulation of the feed concentration allows local increase of AA concentration, which increases the net reaction rate only locally in Zone II. Such a local increase of the reaction rate allows higher purity and recovery while increasing the production rate of PMA at the same time.

So, as discussed herein the production rate of PMA through the raffinate stream outlet decreases with increase in the conversion of AA for both the operating strategies. Thus the higher conversion of AA is not favorable to high production rates of PMA. In addition, it has been found that the process of the present disclosure is more advantageous to obtain high recovery of PMA through the raffinate stream and also for reducing the downstream separation cost compared to the constant feed concentration strategy. Therefore, the process of the present disclosure has significant potential to improve the process performance of the SMBR.

We claim:
1. A process, comprising:
supplying a first reactant and a second reactant to a simulated moving bed reactor (SMBR) at each step of a sequential repeating injection cycle, where the SMBR includes zones each having an injection point and each containing a solid separation media;
reacting the first reactant and the second reactant in the SMBR during the sequential repeating injection cycle to form a first product;
separating the first product in the SMBR with the solid separation media; and changing an amount of one or both of the first reactant and the second reactant injected at one or more of the injection points of the SMBR during a step of the sequential repeating injection cycle.

2. The process of claim 1, where changing the amount of one or both of the first reactant and the second reactant is done at each step of the sequential repeating injection cycle.

3. The process of claim 1, where each step of the sequential repeating injection cycle has a predetermined time ($t_{step}$), and where changing the amount of one or both of the first reactant and the second reactant begins once a first percentage of $t_{step}$ is reached.

4. The process of claim 3, where the first percentage of $t_{step}$ is from 50 percent (%) to less than 100% of $t_{step}$.

5. The process of claim 3, where the first percentage of $t_{step}$ is from 65% to 67% of $t_{step}$.

6. The process of claim 1, where the amount of the first reactant is zero (0) relative a total amount of the first reactant and the second reactant injected at one or more of the injection points of the SMBR.

7. The process of claim 1, where the amount of the first reactant is 100% relative a total amount of the first reactant and the second reactant injected at one or more of the injection points of the SMBR.

8. The process of claim 1, where changing the amount of one or both of the first reactant and the second reactant is done two or more times during a step of the sequential repeating injection cycle.

9. The process of claim 1, where changing the amount of one or both of the first reactant and the second reactant is done as a step change.

10. The process of claim 1, where changing the amount of one or both of the first reactant and the second reactant is done as a linear change.

11. The process of claim 1, where changing the amount includes changing an inlet concentration of one or more of the first reactant and the second reactant injected at one or more of the injection points of the SMBR during each step of the sequential repeating injection cycle.

12. The process of claim 1, where supplying the first reactant to the SMBR includes supplying the first reactant to the SMBR at a stoichiometric excess sufficiently large that the first reactant acts as a desorbent for both a raffinate stream and an extract stream of the SMBR.

13. The process of claim 12, including reacting the second reactant in a stoichiometric deficit relative to the first reactant to extinction in the SMBR.

14. The process of claim 1, including supplying a portion of at least one of the raffinate steam and the extract stream to at least one of the zones of the SMBR.

15. The process of claim 1, where the solid separation media also acts as a catalyst for the reaction of the first reactant and the second reactant.

16. The process of claim 1, where reacting the first reactant and the second reactant in the SMBR during the sequential repeating injection cycle forms the first product and a second product; and where separating the first product in the SMBR with the solid separation media further includes separating the first product from the second product in the SMBR with the solid separation media.

* * * * *